United States Patent
Kyun

Patent Number: 5,178,624
Date of Patent: Jan. 12, 1993

[54] THROW AWAY SCISSORS FOR SEVERING AN UMBILICAL CORD

[76] Inventor: Doo J. Kyun, Room 902, Hyundae Apt. No. 104,, 757 Inhoo 1ka, Dukjin-ku, Jeonjoo-shi, Jeollapukdo, Rep. of Korea

[21] Appl. No.: 720,371

[22] Filed: Jun. 25, 1991

[30] Foreign Application Priority Data

Jan. 15, 1991 [KR] Rep. of Korea ................... 528/91

[51] Int. Cl.$^5$ ............................................. A61B 17/42
[52] U.S. Cl. ...................................... 606/120; 606/174
[58] Field of Search ............... 606/120, 167, 174, 142, 606/205-210; 30/173, 258, 134

[56] References Cited

U.S. PATENT DOCUMENTS

| | | | |
|---|---|---|---|
| 352,245 | 11/1886 | Hullhorst | 606/120 |
| 1,600,225 | 9/1926 | Halpern | 606/174 |
| 1,978,124 | 10/1934 | Batchler | 606/174 |
| 4,938,215 | 7/1990 | Schulman et al. | 606/120 |
| 4,944,092 | 7/1990 | De Groot et al. | 30/134 |
| 5,009,657 | 4/1991 | Cotey et al. | 606/120 |
| 5,046,252 | 9/1991 | Ayuta et al. | 30/258 |

*Primary Examiner*—C. Fred Rosenbaum
*Assistant Examiner*—William W. Lewis
*Attorney, Agent, or Firm*—Spencer, Frank & Schneider

[57] ABSTRACT

This invention relates to an umbilical cord cutting scissors for using one time only in which all portions except blade portion of scissors are replaced by plastic material, or blade portions as well but both blade edges are formed with saw teeth, and semispherical transparent plastic upper and lower container around the blade portions are formed thereof, so that splashing of blood from umbilical cord upon cutting it is prevented, and problem is solved in which umbilical cord is slipped and is not easily cut, and the umbilical cord can be cut hygienically while confirming correct portion of the umbilical cord to be cut off.

The invention is constructed in such a manner that upper blade 10 and lower blades 4a, 4b made of stainless steel are attached respectively into upper recessed "U" shaped recess groove 9 and lower recessed grooves and transparent semispherical lid 6 and container 2 are respectively formed around the blade portions intergrally with scissors 1 main body with upper and lower portions 8a, 8b, 5a, 5b and distance between with lever handles 3, 7 are made so as to be opened approximately to 20°-30° angle at a state that upper blade 10 and lower blades 4a, 4b are engaged each other, and lower blades 4a, 4b are made integrally by resin material equal to the scissors 1 main body, but both blade edges 4a, 4b are made with saw teeth shape.

4 Claims, 2 Drawing Sheets 5,178,624

THROW AWAY SCISSORS FOR SEVERING AN UMBILICAL CORD

BACKGROUND OF THE INVENTION

The present invention relates to a sanitary umbilical cord cutting scissors for using one time only which is made in such a manner that splashing of blood from umbilical cord at the time of umbilical cord cutting of born baby is prevented, umbilical cord is possible to cut off sanitarily while confirming correct portion of umbilical cord to be cut off, and the portion other than blade portion is replaced by a material of transparent PVC group so as to be used for one time only.

Heretofore, since general medical scissors made of linear blade of scissors has been used in maternity clinic in hospital, in case of cutting the umbilical cord, the umbilical cord was slipped along toward tip end direction whereby the cutting of umbilical cord was not easy, and cutting of correct portion of umbilical cord to be cut off was also difficult, and since general medical scissors becomes to re-use while keeping by necessarily sterilizing after using, in case of using a general medical scissors of bad sterilized state, it was unsanitary, in some case, there has been a case that various disease causing from bacterial contamination and the like was occurred at the cut umbilical portion.

And, according to another disadvantage of conventional general medical scissors, because blood within umbilical cord is splashed around instantly to all direction in case when cutting the umbilical cord by clamping both sides of cutting portion by clip upon cutting of umbilical cord, operating gown of operating doctor or nurse and sheet of bed and the like are smeared by blood, and therefore there has been disadvantage that it was inconvenient, unhygienic, uneconomical, and in some case, hepatitis or AIDS and the like are infected to the operating person.

Further, due to a feeling of uneasiness that blood will be splashed to hand or face and operating gown upon cutting the umbilical cord by doctor, the operating person habitually grasps the medical scissors in right hand and shielding the upper side of scissors with left hand and turning a head to sideward then cutting the umbilical cord, therefore there has been also disadvantage that the portion of umbilical cord to be cut was hard to be correctly cut off.

And, in order to prevent that the umbilical cord slips along toward tip end direction of the scissors in case of using the general medical scissors made of linear blade of scissors upon cutting the umbilical cord by operating person, a scissors that both blades of scissors were bent in arcuate form to innerward has been developed, however such scissors also splashes the blood around to every direction upon cutting the umbilical cord by operating person whereby becoming to smear the hand, face, and operating gown of operating person as well as sheet of bed, therefore there has been various disadvantages that it is uneconomical and having a worry about infection of disease and the like.

SUMMARY OF THE INVENTION

Therefore, the present invention is invented to solve such various disadvantages, and it is constructed in such a manner that the material of one(1) upper blade and two(2) lower blades of scissors are made of stainless steel and being formed in saw teeth shape and being formed to be bent in arcuate form to innerward and being formed integrally with scissors main body made of transparent synthetic resin material respectively to middle portions of semispherical upper lid and lower container so as the upper lid to be inserted into the lower container, and cut out portions are formed at both sides of upper lid and lower container, and scissors main body is made of synthetic resin so as to be easily bent so that both lever handles of scissors are opened approximately 20°-30° angle in a state that upper and lower blades are meshed in order to exert strong force to the upper and lower blades of the scissors.

The forgoing and other objects as well as advantages of the present invention will become clear by following description of the invention with reference to the accompanying drawings.

BRIEF DESCRIPTION OF THE DRAWINGS

For a better understanding of the invention, and to show how the same may be carried out into effect, reference will now be made, by way of example, with respect to the accompanying drawings, in which.

DETAILED DESCRIPTION OF THE PREFERRED EMBODIMENTS

Hereinafter, the preferred embodiments according to the present invention will be described in detail with reference to the accompanying drawings as followings.

Figure 1:
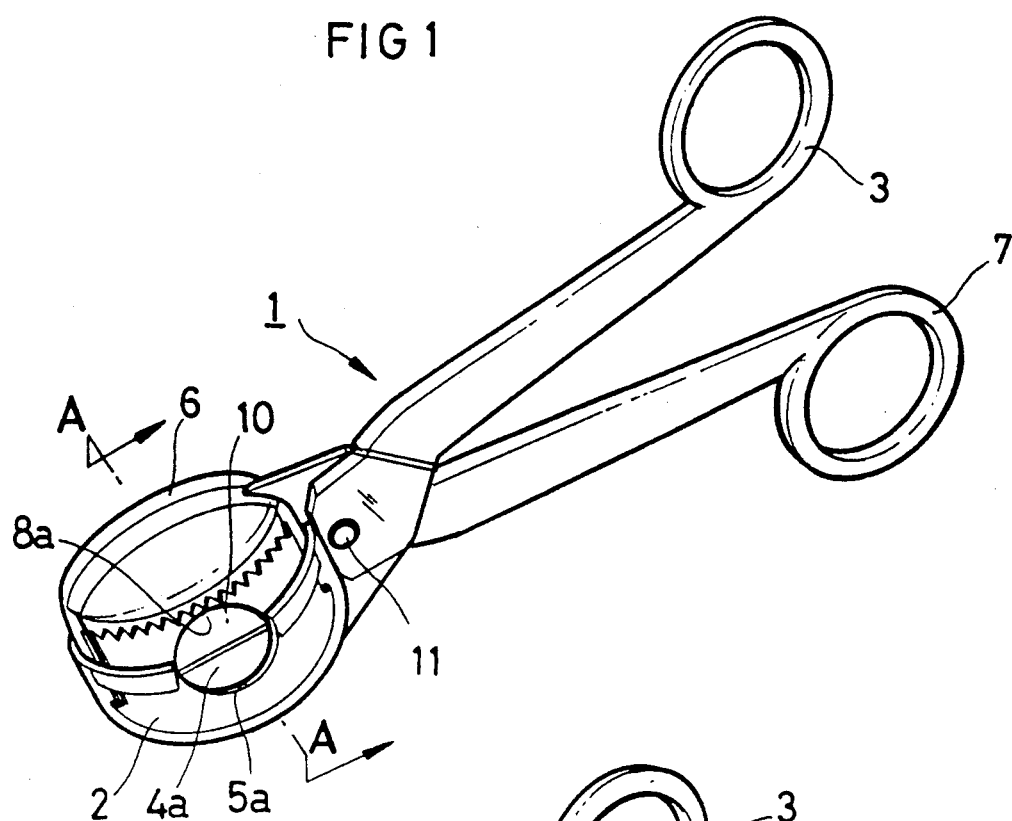
FIG. 1 is a perspective view of a preferred embodiment of the present invention.
Figure 2:
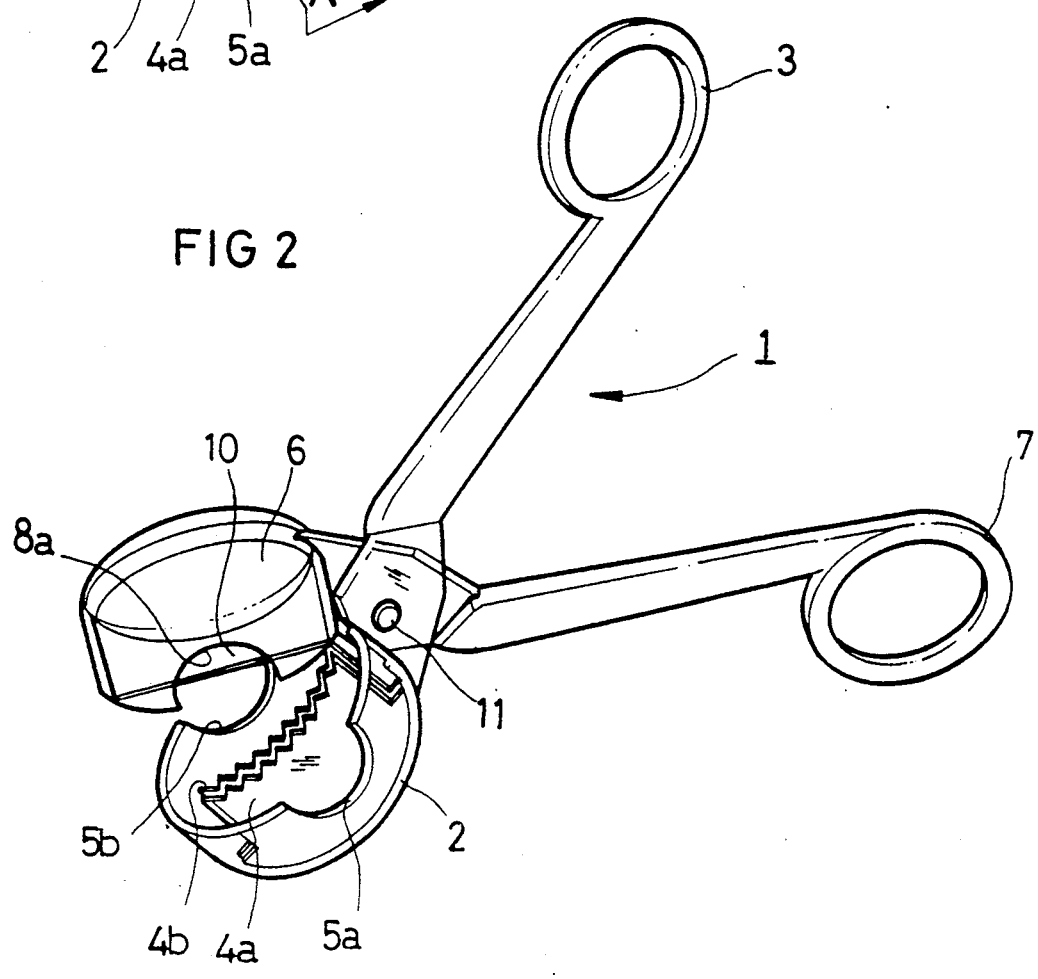
FIG. 2 is a perspective view of a state that an umbilical cord cutting scissors of a preferred embodiment according to the present invention is opened.
Figure 3:
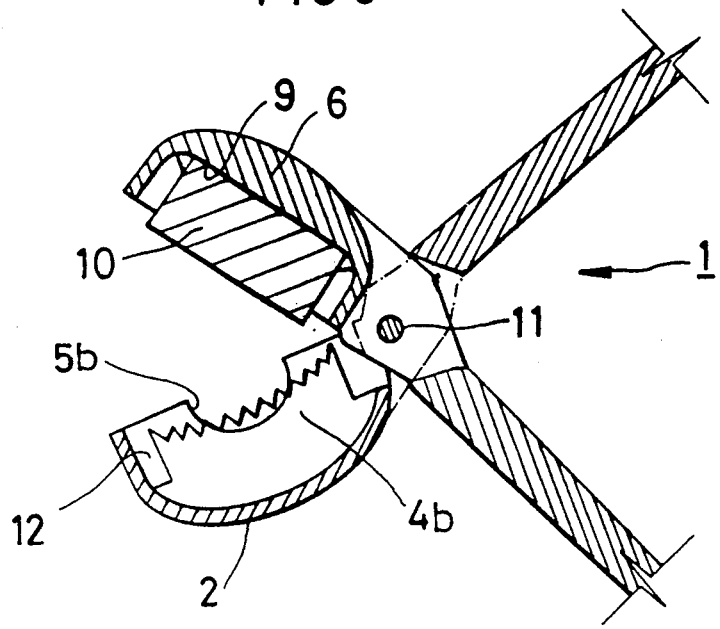
FIG. 3 is a longitudinal cross sectional view for an using state of a preferred embodiment according to the present invention.
Figure 4:
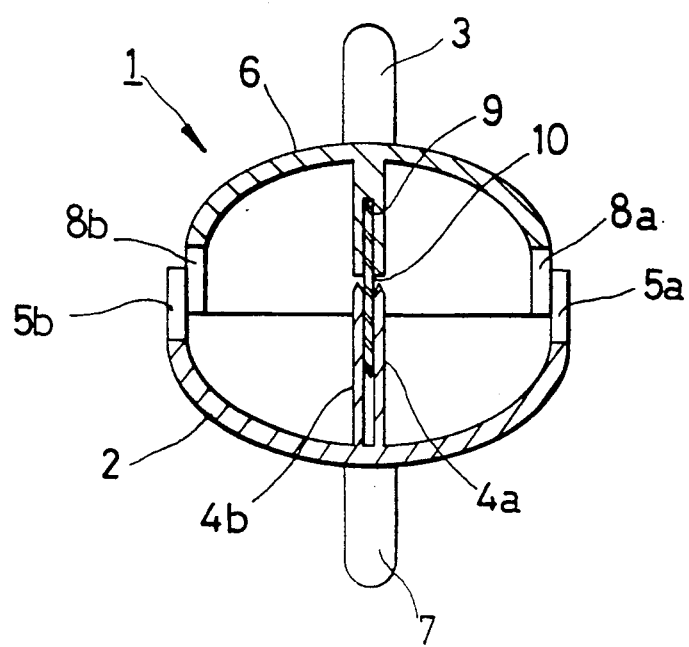
FIG. 4 is a cross sectional view taken along a line A—A of FIG. 1, Throughout the drawings, like reference numerals and symbols are used for designating like or equivalent parts or portions, for simplicity of illustration and explanation.

Referring FIGS. 1 to 4, in a scissors 1 assembled with one upper blade 10 and two lower blades 4a, 4b bent in arcuate form to innerward pivotably fixed by a pivot pin 11, the scissors of the invention is constructed in such a manner that upper recessed "U" shaped recess groove 9 are formed in inner side surface of one upper blade 10 portion and two lower blades 4a, 4b portion of the scissors 1 made of synthetic resin material to which one upper blade 10 and two lower blades 4a, 4b and respectively attached, and upper lid 6 and lower container 2 of semispherical form made of transparent synthetic resin and integrally formed respectively with the scissors 1 main body from the tip ends of upper blade 10 and lower blades 4a, 4b of scissors 1 to adjacent of the pivot pin 11 portion respectively and cut out recess portion 12 is made between the lower container 2 and the blades 4a, 4b tip portion of the scissors 1, and upper cut out portions 8a, 8b and lower cut out portions 5a, 5b are formed respectively to both side portions of the upper lid 6 and lower container 2, so that the two lever handles 3, 7 joined at the pivot pin 11 form an angle of approximately 20°-30° in a state where the upper blade 10 and lower blades 4a, 4b of the scissors 1 closely engage each other.

Operation and effect of thus constructed present invention will be described in detail as followings.

In case of cutting the umbilical cord, while the scissors 1 are opened and the umbilical cord to be cut is placed between the upper cut out portions 8a, 8b and lower cut out portions 5a, 5b, and correct portion of the umbilical cord is confirmed and when the umbilical cord is cut off by pressing the lever handles 3, 7 of the scissors 1, the upper lid 6 is inserted into the cut out recess portion 12 and being engaged within the lower container 2 whereby splashing out of blood spurting from the cut off portion of the umbilical cord is prevented, and since the blood spurted within the upper lid 6 is also collected within the lower container 2, this blood and the scissors 1 itself are thrown away together after one time using and therefore there is effect of convenient and hygienic.

And, as described in above, since the splashing out of the blood is prevented upon cutting the umbilical cord, there is advantage that not only the correct and safe operation can be carried out, but also doctor and nurse can be protected from infection of disease (hepatitis, AIDS and the like) of patient having a worry about occurrence due to the blood of umbilical cord being splashed to all around thereof, and since the umbilical cord cutting scissors of the present invention of which main body of the scissors 1 excluding the one upper blade 10 and two lower blades 4a, 4b as well as pivot pin 11 is formed integrally by transparent synthetic resin material of resin group, its manufacturing is more convenient and its cost is cheaper, and since it becomes to be able to throw away after using only one time, it is very convenient because sterilization at every time upon using the conventional general material scissors is not required or bacterial pollution or infection of diseases causing from poor sterilization can be previously prevented, and since the present invention is also formed with the upper blade 10 and lower blades 4a, 4b by synthetic resin material equal to the scissors 1 main body instead of stainless steel made upper blade 10 and lower blades 4a, 4b, but both blade edges are formed with saw teeth shape, there is effect that the umbilical cord is not entirely slipped upon cutting the umbilical cord.

Furthermore, in order to solve the problem that the umbilical cord is not easily cut due to the main body of the scissors 1 being made of synthetic resin whereby easily bent, it is constructed so as to be opened to approximately 20°-30° angle at a state that the upper blade 10 and lower blades 4a, 4b are engaged each other and when both lever handles 3, 7 are pressed to innerward, and since strong force between the upper lid 6 and lower container 2 according to the principle of lever around the pivot pin 11, the umbilical cord is easily cut off and hence it is very much useful invention.

It will be appreciated that the present invention is not restricted to the particular embodiment that has been described hereinbefore, and that variations and modifications may be made therein without departing from the spirit and scope of the invention as defined in the appended claims and equivalents thereof.

I claim:

1. Scissors for cutting an umbilical cord, comprising
   (a) two handle levers jointed to one another by a pivot pin;
   (b) an upper, hollow, generally hemispherical lid being integral with one of said handle levers and having opposite, lateral cut out portions; the upper lid having an inner supporting groove;
   (c) a generally hemispherical lower container being integral with another of said handle levers and having opposite, lateral cut out portions; in a closed state of the scissors said upper lid and said lower container together defining a generally closed space and said lateral cut out portions of said upper lid form openings of generally closed outline with respective said lateral cut out portions of said lower container for surrounding an umbilical cord extending through said closed space;
   (d) an upper blade fixedly supported in said groove and extending across the upper lid; and
   (e) two lower blades fixedly supported in the lower container and cooperating with the upper blade; said lower blades being arcuate and extending across the lower container; said lower blades cooperating with said upper blade for severing the umbilical cord extending thereacross; said upper blade being in engagement with said lower blades when said handle levers form an angle of approximately 20°-30° with one another.

2. The scissors for cutting an umbilical cord as defined in claim 1, wherein said lower blades and said lower container constitute an integral, one-piece component.

3. The scissors for cutting an umbilical cord as defined in claim 2, wherein said handle levers, said upper lid, said lower container and said lower blades are of a synthetic resin.

4. The scissors for cutting an umbilical cord as defined in claim 3, wherein each said lower blade has a saw-tooth edge.

* * * * *

UNITED STATES PATENT AND TRADEMARK OFFICE
CERTIFICATE OF CORRECTION

PATENT NO. : 5,178,624

DATED : January 12, 1993

INVENTOR(S) : Jae Kyun DOO

It is certified that error appears in the above-identified patent and that said Letters Patent is hereby corrected as shown below:

On the title page, item [76]: Inventor's name should read
—Jae Kyun Doo—.

Signed and Sealed this

Tenth Day of May, 1994

BRUCE LEHMAN

*Attest:*

*Attesting Officer*  *Commissioner of Patents and Trademarks*